United States Patent [19]

O'Meara

[11] Patent Number: 4,580,976

[45] Date of Patent: Apr. 8, 1986

[54] ORTHODONTIC SPRING

[76] Inventor: Anthony J. O'Meara, 11 Chapman Rd., Faulconbridge, Australia, 2776

[21] Appl. No.: 681,046

[22] Filed: Dec. 13, 1984

[30] Foreign Application Priority Data

Jul. 24, 1984 [AU] Australia .............................. PG6195

[51] Int. Cl.⁴ .............................................. A61C 3/00
[52] U.S. Cl. ........................................ 433/21; 433/11; 433/18
[58] Field of Search ....................... 433/21, 22, 18, 10, 433/11, 14, 13

[56]     References Cited

U.S. PATENT DOCUMENTS

| | | | |
|---|---|---|---|
| 3,093,903 | 6/1963 | Kesling | 433/14 |
| 3,237,305 | 3/1966 | Hegedus | 433/21 |
| 3,256,602 | 6/1966 | Broussard et al. | 433/13 |
| 3,262,207 | 7/1966 | Kesling | 433/18 |
| 3,599,331 | 8/1971 | Lee | 433/18 |
| 3,641,672 | 2/1972 | Kesling | 433/21 |
| 3,793,730 | 2/1974 | Begg et al. | 433/21 |
| 3,975,823 | 8/1976 | Sosnay | 433/21 |

Primary Examiner—John J. Wilson
Attorney, Agent, or Firm—Townsend and Townsend

[57]     ABSTRACT

An orthodontic spring assembly including an arch wire, a bracket mounted on the arch wire, an orthodontic spring mounted in the bracket and resiliently deformed so as to apply a force to the tooth so as to correct axial inclination thereof.

5 Claims, 12 Drawing Figures

ORTHODONTIC SPRING

The present invention relates to an orthodontic device to correct the axial inclination of teeth.

Conventional orthodontic bridge assemblies have been difficult to install and do not readily lend themselves to the application of a correcting torque to select teeth.

It is the object of the present invention to overcome or substantially ameliorate the above disadvantages.

There is disclosed herein an orthodontic spring assembly comprising a bracket to be fixed to a tooth and through which an arch wire is to pass, a spring supported by said bracket and adapted to engage said tooth to correct the axial inclination thereof, said spring having a base portion received in said bracket and an armature resiliently deformable so as to be biased into engagement with said tooth so as to apply a force thereto to correct the axial inclination of the tooth.

There is also disclosed herein an orthodontic spring formed of resilient metal wire bent about several axes transverse of the wire so as to provide a base and an armature fixed thereto, and wherein said base provides a shank received by a bracket engaging an arch wire and said armature defines a plane inclined to said shank.

Still further, there is disclosed herein an orthodontic spring formed of resilient metal wire bent about several transverse axes so as to provide a base to be attached to an arch wire by a bracket, and wherein said wire has an end forming said armature, said end having a hook to engage said arch wire to thereby resiliently deform said spring so as to bias said armature into contact with a tooth.

A preferred form of the present invention will now be described by way of example with reference to the accompanying drawings wherein.

Figure 1:
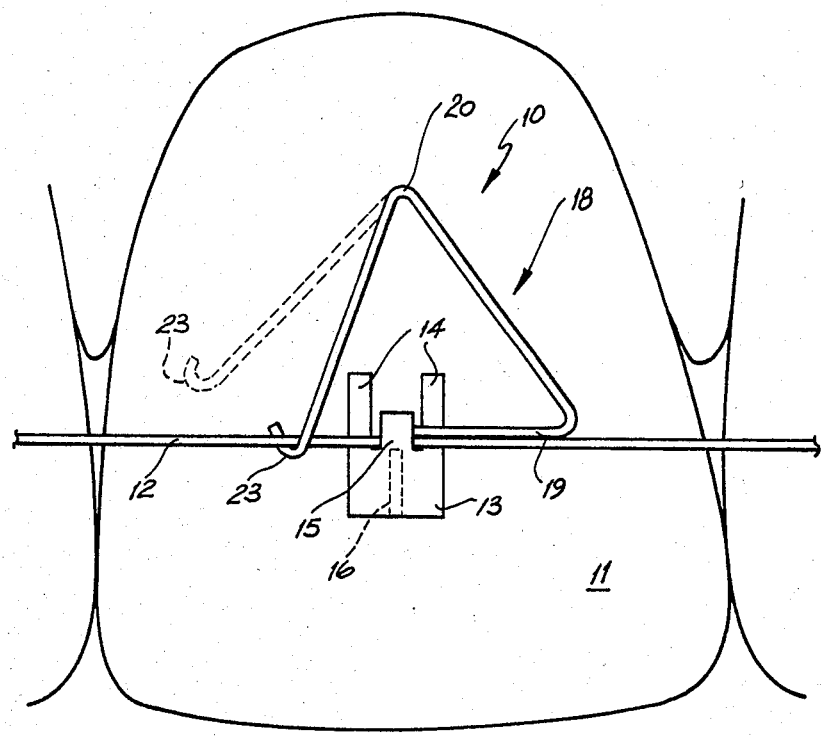
FIG. 1 is a schematic front elevation of an orthodontic device applied to a tooth.

In FIG. 1 there is schematically depicted an orthodontic device 10 applied to a tooth 11. The orthodontic device 10 includes an arch wire 12 which passes through a bracket 13 fixed to the tooth 11. The bracket 13, in conventional form, is provided with two spaced legs 14 which abut the tooth 11 and a projection 15 spaced from the legs 14 so that the arch wire 12 passes between the legs 14 and projection 15. The bracket 13 is also provided with a passage 16.

The orthodontic device 10 further includes a spring 18 including a base portion 19 and an armature portion 20. The spring 18 is formed of metal wire bent about several transverse axes so as to provide the configuration depicted.

Figure 2:
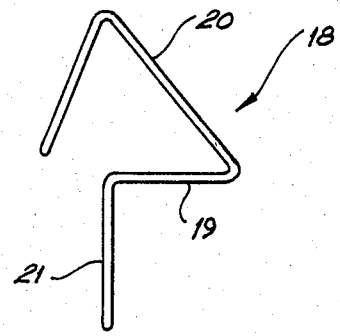
FIG. 2 is a schematic front elevation of a spring employed in the device of FIG. 1.
Figure 3:
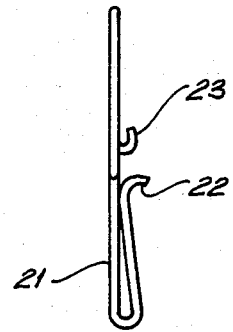
FIG. 3 is a schematic side elevation of the spring of FIG. 2.
Figure 4:
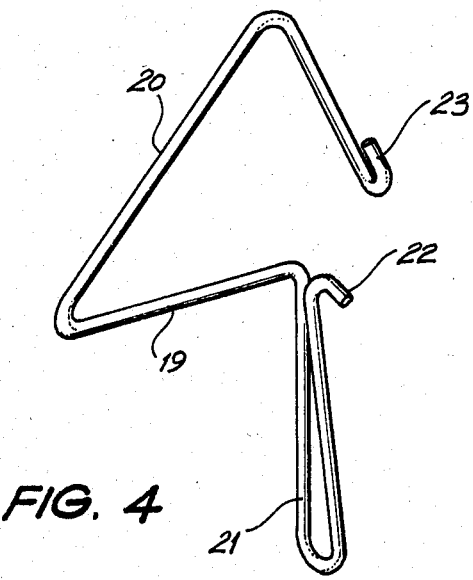
FIG. 4 is a schematic perspective view of the spring of FIGS. 2 and 3.

Now with reference also to FIGS. 2 to 4, the spring 18 is also provided with a fixing leg 21 terminating with a projection 22. The armature 20 terminates in a hook 23. The spring 18 is formed from a length of metal wire bent about several transverse axes so as to provide the leg 21 and armature 20. It should further be appreciated that the hook 23 is spaced vertically from the base 19.

The abovedescribed spring 18 acts to correct the axial inclination of the tooth 11 by resilient deformation of the spring 18. More particularly with reference to FIG. 1, the spring 18 is depicted in dashed lines in the inoperative mode. However, the spring 18 is also depicted in an operative position with the hook 23 passing under the arch wire 12. When the spring 18 is resiliently deformed from the inoperative to the operative position, the armature 20 is resiliently biases towards the tooth 11, commonly known as applying a lingual torque to the tooth. This resilient biasing of the armature, 20 applies a force to the tooth 11 to correct lingual axial inclination thereof.

The leg 21 acts to secure the spring 18 in position by being located in passage 16 while the projection 22 passes over the arch wire to retaining the arch wire in position.

Now with reference to FIGS. 5 to 8, there is schematically depicted an orthodontic device 30 applied to a tooth 31. The device 30 includes a bracket 32 fixed to the tooth 31 and through which passes an arch wire 33. The bracket 32 has two spaced legs 34 which abut the tooth 31, and a bracket 35 spaced from the legs 34 to enable the arch wire 33 to pass between the legs 34 and projection 35. The bracket 32 is also provided with a passage to receive a fixing pin 36 in a conventional manner.

The orthodontic device 30 further includes a spring 37 which comprises a base 38 and an armature being formed by two armature lugs 39.

Figure 6:
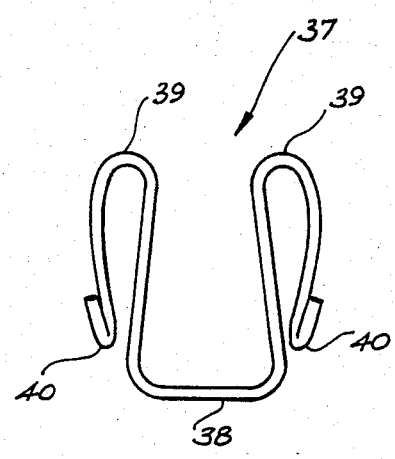
FIG. 6 is a schematic front elevation of a spring employed in the device of FIG. 5.
Figure 7:
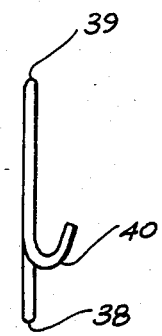
FIG. 7 is a schematic side elevation of the spring of FIG. 6.
Figure 8:
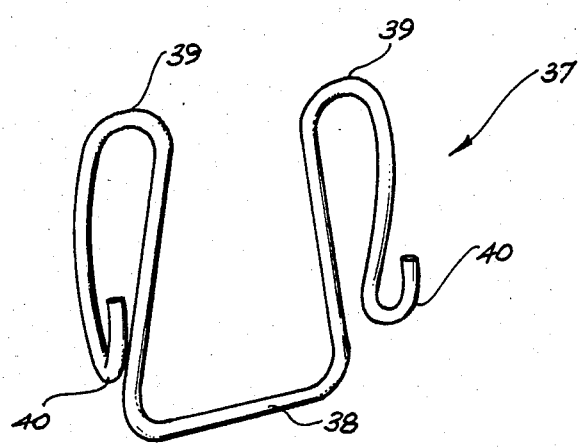
FIG. 8 is a schematic perspective view of the spring of FIGS. 6 and 7.
Figure 9:
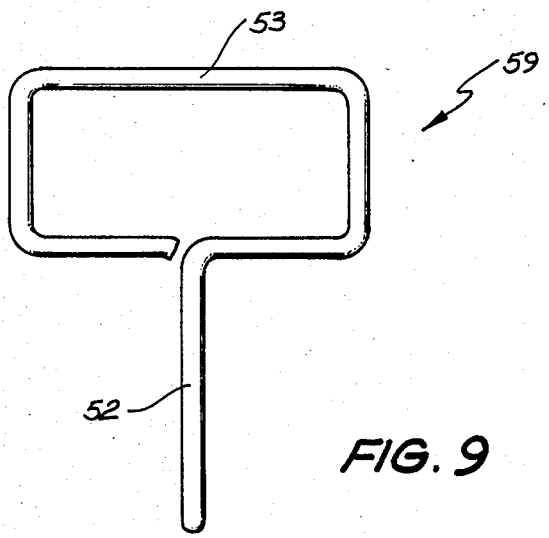
FIG. 9 is a schematic elevation of a spring to apply force to a tooth to correct the axial inclination thereof.
Figure 10:
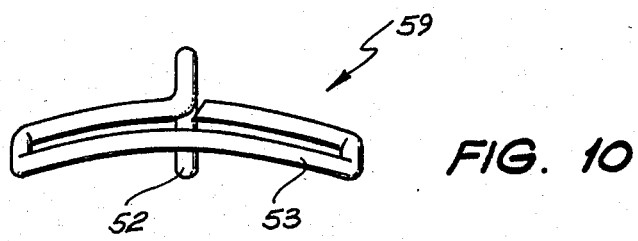
FIG. 10 is a schematic plan view of the spring of FIG. 1.
Figure 11:
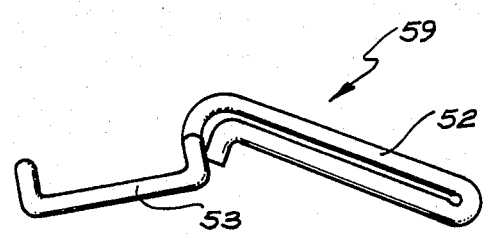
FIG. 11 is a schematic side elevation of the spring of FIG. 1.

Now with particular reference to FIGS. 6 to 8, the spring 37 is bent about several transverse axes so as to provide the base 38 and armature lugs 39 defined by two loops. The armature lugs 39 terminate in hooks 40. In a similar manner to the embodiment of FIGS. 1 to 4, the base 38 of the spring 37 is also mounted in between the legs 34 and projection 35 and is secured in position by means of the pin 36.

Figure 5:
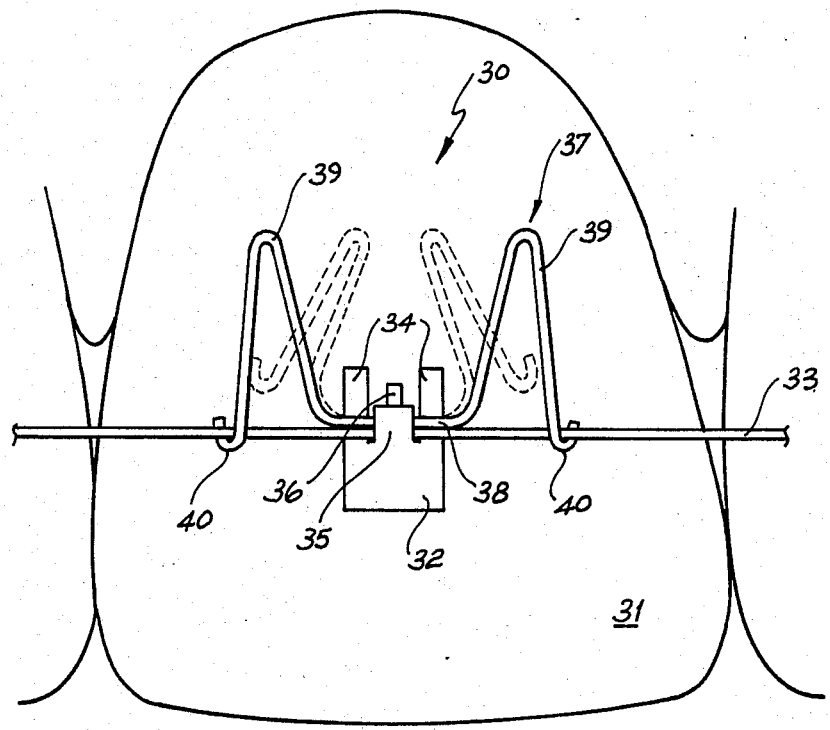
FIG. 5 is a schematic front elevation of an orthodontic device applied to a tooth.

In FIG. 5, the spring 37 is depicted, in dashed lines, in the inoperative position. In moving the spring 37 to the operative position, the armature lugs 39 are resiliently deformed so that the springs 40 pass underneath the arch wire 33. When the armature lugs 39 are deformed, they become resiliently biased against the tooth 37 so as to apply a force thereto to correct the axial inclination of the tooth 31.

In FIGS. 9 to 12 there is schematically depicted an orthodontic spring assembly 50 which is to be applied to a tooth 51 to correct the axial inclination thereof by applying a force to the tooth 51. The spring assembly 50 includes a spring 59 having a shank 52 and an armature 53 which head 53 is defined by a loop of generally rectangular configuration. Preferably the spring assembly 57 is formed from a length of resilient wire bent about several transverse axes so as to provide the configuration illustrated in FIGS. 9 to 11. In particular it should be noted, as can be seen from FIG. 11, that the armature 53 defines a plane inclined at an angle to the shank 52 so that the armature 53 may be brought into engagement with the tooth. By deflecting the armature 53 relative to the shank 52, the armature 53 is resiliently biased into engagement with the tooth to thereby apply force to the tooth.

Figure 12:
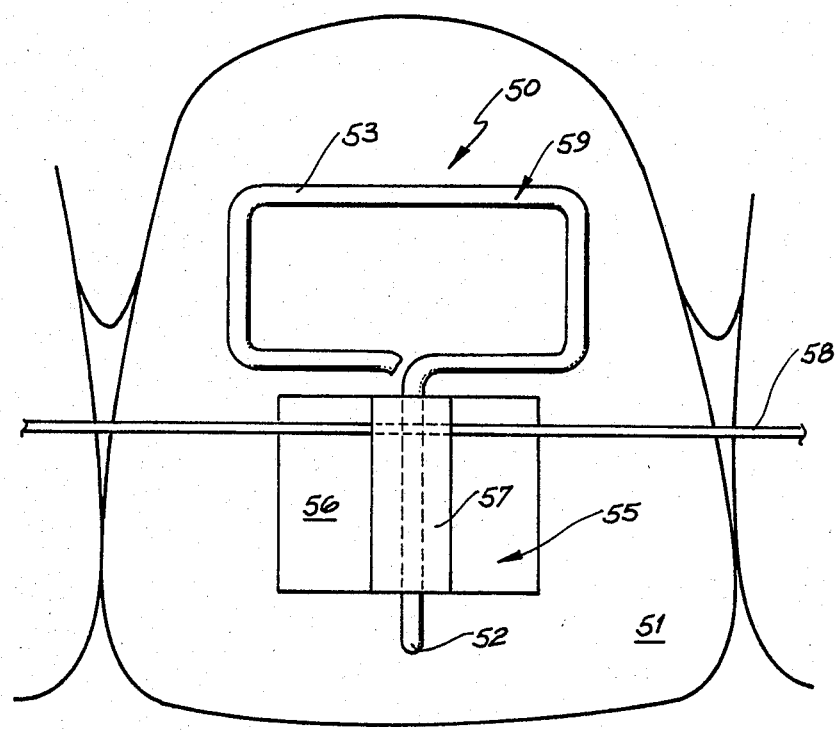
FIG. 12 is a schematic elevation depicting the spring of FIG. 1 applied to a tooth.

Turning now in particular to FIG. 12 wherein the spring 59 is illustrated as being supported in a holder 55 so that the armature 53 is biased into engagement with the tooth 51 as discussed above. The support 55 includes a base 56 from which extends a flange 57 having a passage 58 through which the shank 52 passes. Also extending through the flange 57 is a wire 58 which extends around the teeth so as to retain the support 55 in abutting relationship with respect to the tooth 51.

It is preferred that the shank 52 is slidably received within the passage 58 so that the head can turn about the axis of the shank 52 to adjust to the orientation of the tooth.

What is claimed is:

1. An orthodontic spring mounted in a bracket to be fixed to a tooth and through which bracket an arch wire extends, said spring consisting of metal wire bent about several axes transverse of the wire so as to provide a shank received within said bracket and a heat portion for abutting said tooth, said head portion having a termainal end provided with a hook to securely engage said arch wire, said head being movable from a non-operative position with said hook disengeged with respect to said arch wire and not applying an effective force to said tooth, to an operative position with said heat resiliently biased into engagement with said tooth so as to apply a force thereto to correct lingual axial inclination thereof, which force results from resilient deformation of said heat by said hook being brought into engagement with said arch wire.

2. The orthodontic spring of claim 1 wherein said head portion is of a generally rectangular configuration thereby having a base and two sides, with one of said sides being provided with said terminal end and said shank extending from said base in a direction generally normal thereto.

3. The orthodontic spring of claim 2 wherein said shank is generally linear and is provided by a looped portion of said wire terminating with a projection which retains the arch wire withn the bracket.

4. An orthodontic spring mounted in a bracket to be fixed to a tooth and through which bracket an arch wire extends, said spring comprising metal wire bent about several transverse axes so as to provide a base received within said bracket and a pair of armature lugs for abutting said tooth, each armature lug having a terminal end provided with a hook to securely engage said arch wire, each lug being movable from a non-operative position with its hook disengaged with respect to said arch wire so as to apply an effective force to said tooth, to an operative position with the armature lug resiliently biased into engagement with said tooth so as to apply a force thereto to correct lingual axial inclination thereof, which force results from resilient deforamtion of the armature lug by placing the hook thereof into engagement with said arch wire.

5. The orthodontic spring of claim 4 wherein said base is generally linear so as to extend generally parallel to said arch wire and each of said lugs is of a generally rectangular configuration.

* * * * *